(12) United States Patent
Helland

(10) Patent No.: US 7,027,852 B2
(45) Date of Patent: Apr. 11, 2006

(54) LEAD WITH DISTAL TIP SURFACE ELECTRODES CONNECTED IN PARALLEL

(75) Inventor: John R. Helland, Saugus, CA (US)

(73) Assignee: Pacesetter, Inc., Sylmar, CA (US)

(*) Notice: Subject to any disclaimer, the term of this patent is extended or adjusted under 35 U.S.C. 154(b) by 588 days.

(21) Appl. No.: 10/153,848

(22) Filed: May 21, 2002

(65) Prior Publication Data

US 2003/0220676 A1 Nov. 27, 2003

(51) Int. Cl.
*A61B 5/042* (2006.01)
*A61N 1/05* (2006.01)

(52) U.S. Cl. .................. 600/375; 600/374; 607/127

(58) Field of Classification Search ........ 600/372–375, 600/377, 381; 607/115–116, 119, 123, 125–127, 607/131
See application file for complete search history.

(56) References Cited

U.S. PATENT DOCUMENTS

| | | | |
|---|---|---|---|
| 3,815,611 A | 6/1974 | Denniston, III | 128/419 D |
| 4,154,247 A | 5/1979 | O'Neill | 128/419 P |
| 4,365,639 A | 12/1982 | Goldreyer | 128/786 |
| 4,513,752 A | 4/1985 | Weyant | 128/696 |
| 4,848,352 A * | 7/1989 | Pohndorf et al. | 600/374 |
| 4,998,975 A | 3/1991 | Cohen et al. | 128/419 D |
| 5,050,601 A | 9/1991 | Kupersmith et al. | 128/419 D |
| 5,144,960 A | 9/1992 | Mehra et al. | 128/786 |
| 5,306,292 A | 4/1994 | Lindegren | 607/11 |
| 5,342,414 A | 8/1994 | Mehra | 607/127 |
| 5,370,665 A * | 12/1994 | Hudrlik | 607/9 |
| 5,374,287 A | 12/1994 | Rubin | 607/131 |
| 5,466,254 A | 11/1995 | Helland | 607/123 |
| 5,476,496 A | 12/1995 | Strandberg et al. | 607/122 |
| 5,545,201 A * | 8/1996 | Helland et al. | 607/127 |
| 5,849,032 A | 12/1998 | Van Venrooij | 607/123 |
| 5,871,531 A * | 2/1999 | Struble | 607/126 |
| 6,064,905 A | 5/2000 | Webster et al. | 600/424 |
| 6,085,119 A | 7/2000 | Scheiner et al. | 607/122 |
| 6,094,596 A | 7/2000 | Morgan | 607/5 |
| 6,146,338 B1 | 11/2000 | Gardeski et al. | 600/585 |
| 6,181,972 B1 * | 1/2001 | Guedeney et al. | 607/121 |
| 6,195,586 B1 | 2/2001 | Kuzma | 607/137 |
| 6,249,708 B1 | 6/2001 | Nelson et al. | 607/122 |
| 6,501,994 B1 * | 12/2002 | Janke et al. | 607/127 |
| 6,526,321 B1 * | 2/2003 | Spehr | 607/116 |
| 6,609,027 B1 * | 8/2003 | Kroll et al. | 607/9 |
| 2003/0204232 A1 * | 10/2003 | Sommer et al. | 607/122 |

FOREIGN PATENT DOCUMENTS

| | | |
|---|---|---|
| EP | 0919254 A2 | 2/1999 |
| WO | WO 99/15231 | 1/1999 |
| WO | WO 99/55411 A2 | 4/1999 |
| WO | WO 99/55411 A3 | 4/1999 |

* cited by examiner

*Primary Examiner*—Robert E. Pezzuto
*Assistant Examiner*—Kristen Mullen

(57) ABSTRACT

An body implantable stimulation lead is provided including tip electrode patterns and configurations producing low noise, clean sensed signals devoid of far field components, such sensed signals being generated irrespective of the direction of the incident depolarization wavefront. The invention also provides high pacing impedances and advantageous anode-to-cathode surface area ratios. Further, implantable leads utilizing the features of the present invention are particularly suitable for left side stimulation therapies.

28 Claims, 9 Drawing Sheets

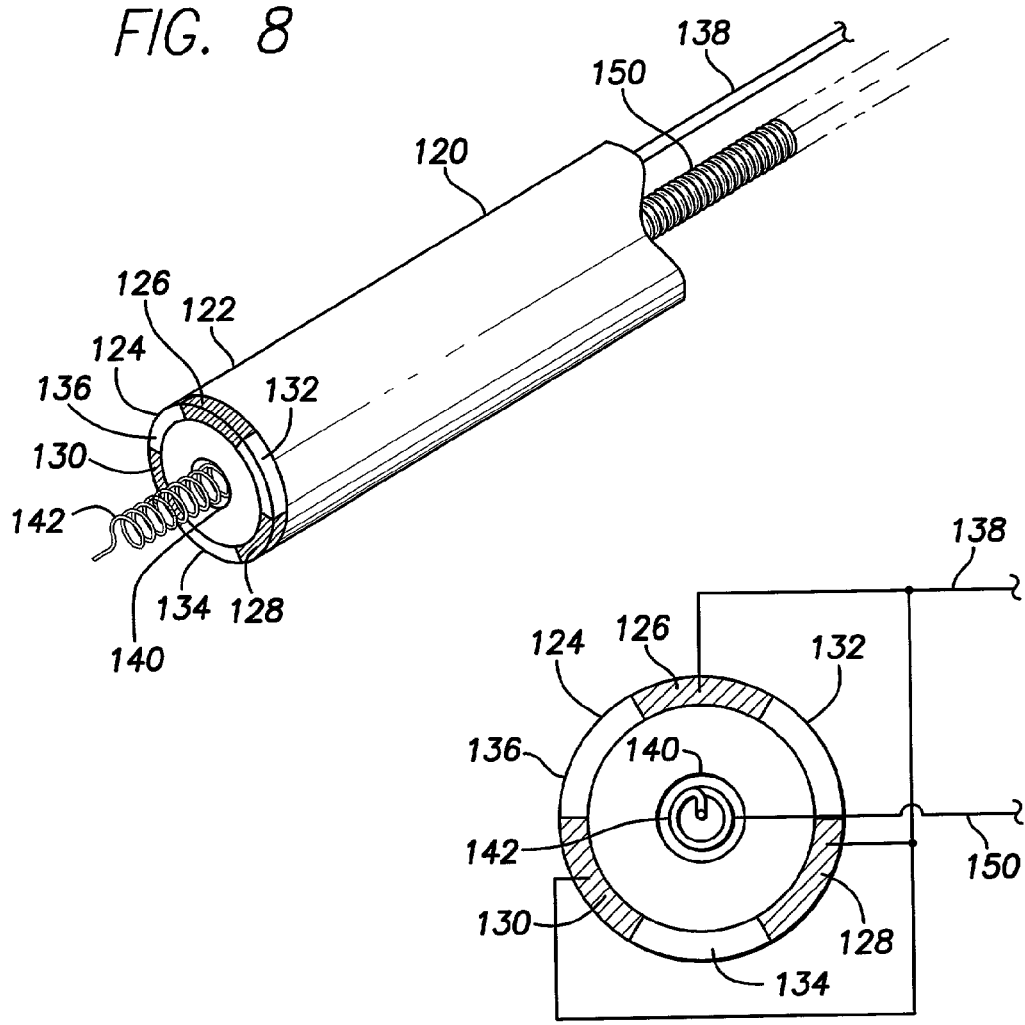
FIG. 8
FIG. 9
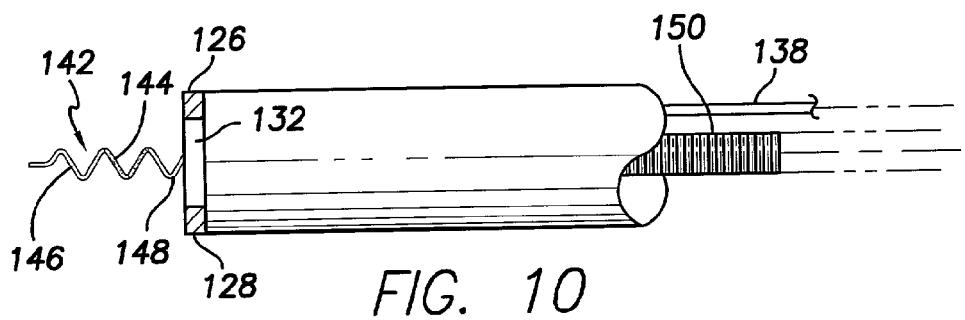
FIG. 10

LEAD WITH DISTAL TIP SURFACE ELECTRODES CONNECTED IN PARALLEL

FIELD OF THE INVENTION

The present invention relates generally to body implantable leads, such as bipolar endocardial pacing and sensing leads, and more particularly to improved electrode arrangements for such leads.

BACKGROUND OF THE INVENTION

1. Far Field Signals

Unipolar or bipolar cardiac pacemaker lead systems fulfill two functions. The first function is to provide an electrical conduit by which a pacemaker output pulse is delivered to stimulate the local tissue adjacent to the distal tip of the lead. The second function is to sense local, intrinsic cardiac electrical activity that takes place adjacent to the distal end of the lead.

One of the problems with body implantable pacing and sensing lead systems is their inability to suppress or attenuate the voltage levels of far field electrical signals. These signals are generated by depolarizations of body tissues in areas remote from the local sensing site and are manifested as propagated voltage potential wavefronts carried to and incident upon the local sensing site. For example, a far field signal may comprise the intrinsic signal originating from the chamber of the heart opposite the one in which the lead electrode is located. Thus, where the lead electrode is implanted in the atrium, the ventricular QRS-wave comprises a far field signal; in contrast, for a ventricular implanted electrode, the atrial P-wave is the far field signal. The sensing electrodes detect or sense the voltages of these signals and interpret them as depolarization events taking place in the local tissue when such polarizations are above the threshold sensing voltage of the system. When far field signal voltages surpassing the threshold voltage are applied to the sensing circuitry of the pulse generator or pacemaker, activation of certain pacing schemes or therapies can be erroneously triggered.

With the development of universal stimulation/sensing systems, that is, three and four chamber combination pacemaker/cardioverter/defibrillators, accurate sensing of cardiac signals has become even more critical, and management, suppression, and/or elimination of far field signals is vitally important to allow appropriate device algorithms to function without being confused by the undesirable far field signals. As noted, an error in sensing can result in either a wrongfully delivered therapy or a wrongfully withheld therapy.

Approaches to the problem of far field signal sensing include configuring the circuitry of the pacemaker to attenuate far field signals, and introducing a blanking period long enough to prevent the sensing of unwanted signals. These solutions are described in U.S. Pat. No. 4,513,752 assigned to the owner of the present invention.

2. Net Signal Amplitude between Sensing Electrodes

U.S. Patent No. 5,306,292 teaches the use of multiple small electrodes on a lead tip for pacing and/or sensing. Each electrode has its own dedicated conductor and pacemaker connector terminal. The '292 patent discloses a scheme for selecting the best combination of electrodes for pacing and/or sensing. However, if two electrodes are selected for sensing a problem arises: For any two electrodes selected an orthogonal wavefront impinging on the two electrodes would result in a null output signal, that is, a net sensed signal having an amplitude of virtually zero volts which therefore would not be sensed by the device's circuitry.

U.S. Pat. No. 6,064,905 discloses a multi-element temporary mapping catheter including a plurality of small electrodes disposed about a tip section. As in the '292 patent, the electrodes in the '905 patent are each connected to a separate conductor. Accordingly, as in the '292 patent, a depolarization wavefront orthogonally incident on any pair of electrodes can result in a substantially zero net voltage signal. This is true also of the sensing electrode arrangement disclosed in U.S. Pat. No. 4,365,639 in which the electrodes are carried about the side surface of the lead body.

3. Ratio of Anode-to-Cathode Surface Areas

As illustrated by U.S. Pat. No. 5,476,496, it is known that in a bipolar pacing and sensing lead, the indifferent electrode or anode, typically in the form of a conductive ring disposed proximally of the tip electrode (which serves as the cathode), should have a large active surface area compared to that of the cathode. The objects of such an areal relationship are to reduce the current density in the region surrounding the anode so as to prevent needless or unwanted stimulation of body tissue around the anode when a stimulation pulse is generated between the cathode and anode, and to minimize creation of two focal pacing sites, one at the cathode and one at the anode which could promote arrhythmia. Typically, the total surface area of the anode is selected so as to be about two times to about six times that of the cathode.

4. Pacing Impedance

The design of a stimulation electrode typically carried at the distal tip of a body implantable lead must satisfy various requirements. An essential requirement is that a high impedance be provided at the tissue/electrode interface so as to decrease the current necessary for stimulation and consequently to increase the life span of the pulse generator battery without being electrically inefficient. A simple way to efficiently increase the interface impedance is to reduce the area of the active surface of the stimulation electrode. A relatively high impedance, for example, about 1,000 ohms, is a typical target value. (See, for example, U.S. Pat. No. 6,181,972.)

5. Left Side Stimulation and Sensing

The advantages of providing pacing therapies to both the right and left heart chambers are well established. For example, in four chamber pacing systems, four pacing leads, typically bipolar leads, are positioned for both pacing and sensing in the respective heart chambers. To provide left side stimulation and sensing, leads are transvenously implanted in the coronary sinus region, for example, in a vein such as the great vein, the left posterior ventricular (LPV) vein, or other coronary veins, proximate the left ventricle of the heart. Such placement avoids the risks associated with implanting a lead directly within the left ventricle which can increase the potential for the formation of blood clots which may become dislodged and then carried to the brain where even a small embolism could cause a stroke. As used herein, the phrase "coronary sinus region" refers to the coronary sinus, great cardiac vein, left marginal vein, left posterior ventricular vein, middle cardiac vein, and/or small cardiac vein or any other coronary vein accessible by way of the coronary sinus.

The tip electrode of a lead implanted in the coronary sinus region can pace and sense left side ventricular activity. When such a lead includes a second electrode proximal of the tip electrode and residing in the coronary sinus above the left ventricle closely adjacent to the left atrium of the heart, pacing and sensing of left atrial activity is made possible. Moreover, the lead may include one or more electrodes for the delivery of electrical shocks for terminating tachycardia and/or fibrillation. Such cardioverting/defibrillating electrodes may be used by themselves or may be combined with pacing and/or sensing electrodes.

SUMMARY

Broadly, the present invention provides tip electrode patterns and configurations producing low noise, clean sensed signals devoid of far field components, such sensed signals being generated irrespective of the direction of the incident depolarization wavefront. The invention also provides high pacing impedances and advantageous anode-to-cathode surface area ratios. Further, implantable leads utilizing the features of the present invention are particularly suitable for left side stimulation therapies.

In accordance with one specific, exemplary embodiment of the invention, there is provided an implantable stimulation lead for transmitting electrical signals between an implantable medical device and selected body tissue, the lead comprising a proximal end carrying a connector assembly connectable to the implantable medical device; a distal end; and at least one electrode of a first polarity carried by the distal end of the lead and adapted to electrically communicate with the selected body tissue. The lead further comprises at least two electrodes of a second polarity carried by the distal end of the lead and adapted to electrically communicate with the selected body tissue. A housing of insulating material couples the proximal and distal ends of the lead and a first electrical conductor enclosed within the housing electrically couples the at least one electrode of the first polarity with a first terminal on the connector assembly. A second electrical conductor enclosed within the housing electrically couples the at least two electrodes of the second polarity with a second terminal on the connector assembly.

In accordance with another aspect of the invention, the at least one electrode of the first polarity and the at least two electrodes of the second polarity comprise electrodes for sensing local electrical activity manifested by an incident depolarization wavefront. Further, the at least one electrode of the first polarity and the at least two electrodes of the second polarity are arranged on the distal end in a non-aligned pattern whereby an output voltage signal of sufficient amplitude to be acknowledged by the implantable medical device is generated between the at least one electrode of the first polarity, on the one hand, and the at least two electrodes of the second polarity, on the other hand, irrespective of the direction of an incident depolarization wavefront. All of the electrodes are preferably arranged in a closely spaced cluster so as to sense local electrical events within the selected body tissue and not far field signals. Still further, the at least one electrode of the first polarity may comprise a cathode and the at least two electrodes of the second polarity may collectively comprise an anode. Preferably, the at least two anode electrodes have a total surface area greater than the surface area of the least one cathode electrode, and the electrodes have surface areas providing an impedance of at least about 1,500 ohms.

In accordance with yet another aspect of the invention, the distal end of the lead carries an extendable/retractable screw-in helix for anchoring the distal end. Preferably, the screw-in helix has an electrically conductive portion, a third electrical conductor coupling the screw-in helix to a third terminal on the connector assembly. Where the selected body tissue comprises a heart, the distal end of the lead may be configured to passively anchor the distal end within a coronary vessel overlying the left side of the heart.

Pursuant to another specific, exemplary embodiment of the invention, there is provided a body implantable lead for transmitting electrical signals between an electrical connector at a proximal end of the lead and selected body tissue, the electrical connector being adapted to be received by a receptacle in an implantable medical device. The lead comprises a distal end including a tip and a side surface, the side surface carrying at least two parallel-connected electrodes jointly functioning as an anode, and further carrying at least one electrode functioning as a cathode, the anode and cathode electrodes being positioned proximally of the tip and adapted to electrically communicate with the selected body tissue. A first conductor electrically couples the at least two parallel-connected anode electrodes with a first contact on the connector assembly and a second conductor electrically couples the at least one cathode electrode with a second contact on the connector assembly.

Preferably, the anode and cathode electrodes on the side surface of the distal end are configured and positioned to generate a net voltage output in response to an incident depolarization wavefront, the net voltage output being sufficient to be acknowledged by the implantable medical device. Further, the anode and cathode electrodes may be arranged on the side surface so as to generate the net voltage output irrespective of the direction of the incident depolarization wavefront. Still further, the at least two anode electrodes preferably have a total active surface area greater than the total active surface area of the at least one cathode electrode, and all of the electrodes are preferably arranged in a closely spaced cluster so as to sense local electrical events within the selected body tissue and not far field signals.

BRIEF DESCRIPTION OF THE DRAWINGS

The foregoing and other objects, features and advantages of the invention will be evident to those skilled in the art from the detailed description below, taken together with the accompanying drawings, in which:

FIG. 8 is a perspective view of a portion of the distal end of a bipolar endocardial pacing and sensing lead having a distal tip incorporating an electrode array in accordance with yet another embodiment of the present invention;

FIG. 9 is a front elevation view of the lead shown in FIG. 8;

FIG. 10 is a side view of the distal end of the lead shown in FIG. 8;

DETAILED DESCRIPTION

The following description presents preferred embodiments of the invention representing the best mode contemplated for practicing the invention. This description is not to be taken in a limiting sense but is made merely for the purpose of describing the general principles of the invention whose scope is defined by the appended claims. Moreover, the context in which the invention is principally shown and described herein, that is, bipolar pacing and sensing leads, is illustrative only; it will be understood by those skilled in the art that the invention has applicability to a wide variety of body implantable lead types.

Figure 1:
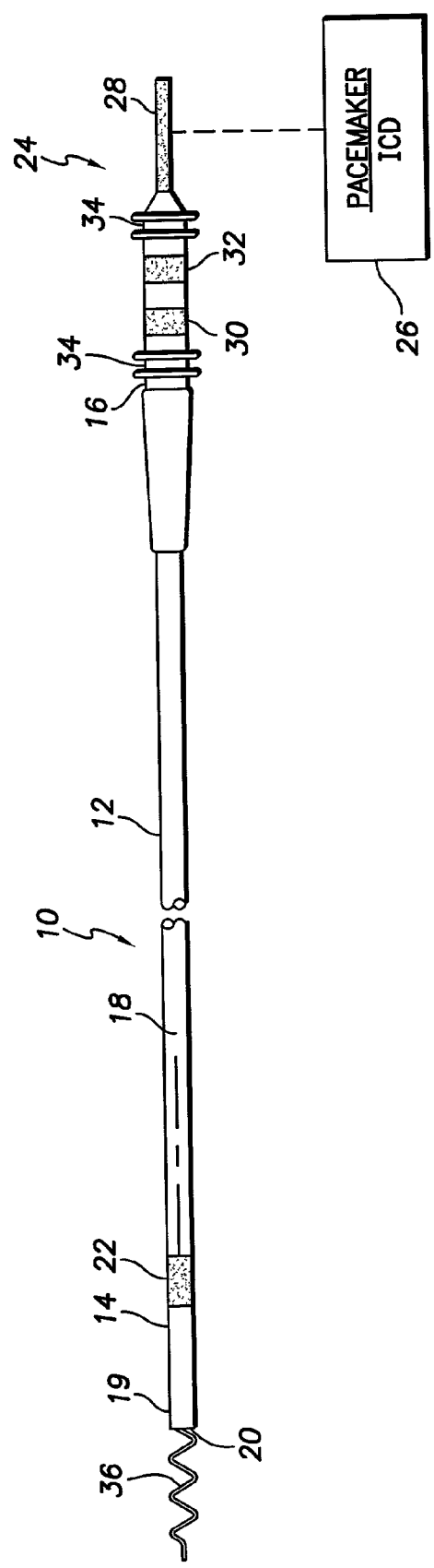
FIG. 1 is side view of a bipolar endocardial pacing and sensing lead system incorporating the present invention.
Figure 2:
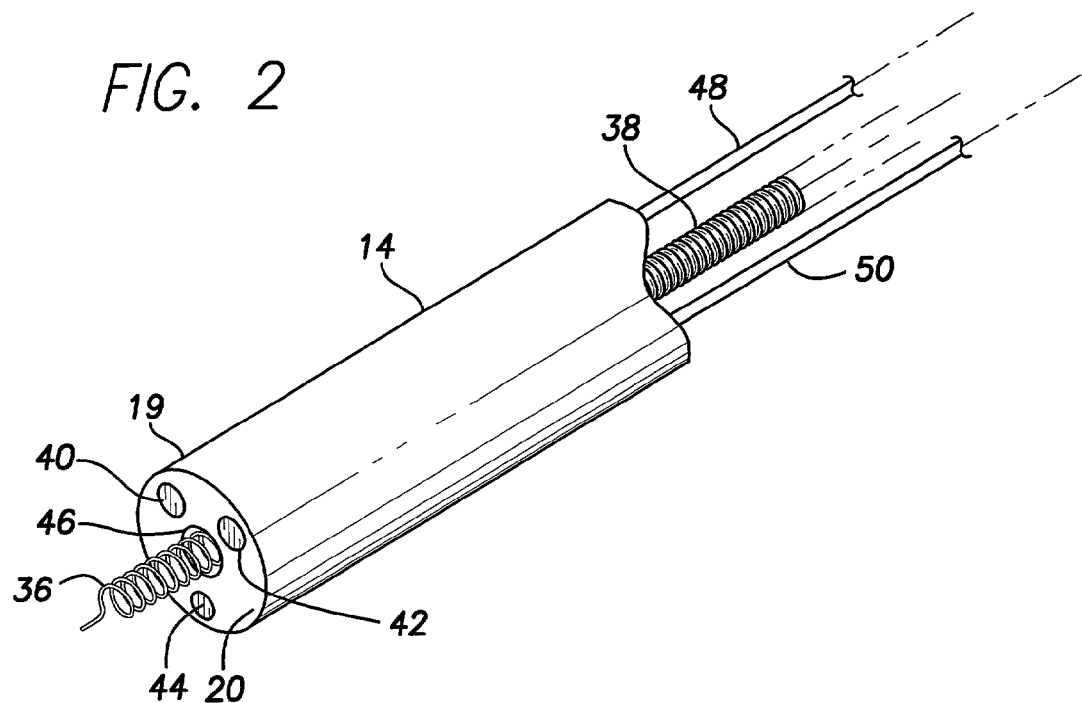
FIG. 2 is a perspective view of a portion of the distal end of a bipolar endocardial pacing and sensing lead including a distal tip carrying an electrode array in accordance with one specific exemplary embodiment of the present invention.
Figure 3:
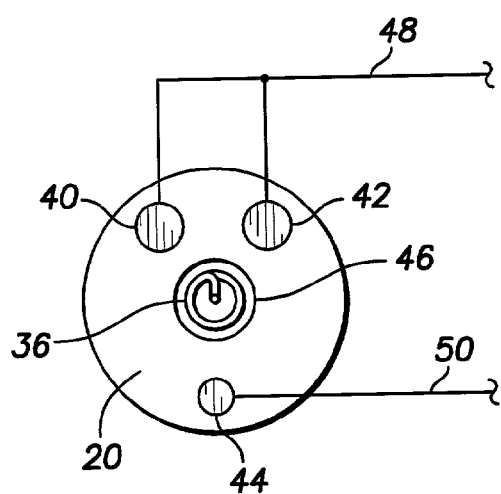
FIG. 3 is a front elevation view of the lead of FIG. 2.

With reference to FIGS. 1–3, there is shown a bipolar endocardial pacing and sensing lead 10 in accordance with a preferred embodiment of the present invention. The lead 10 includes a lead body 12 comprising a distal end 14 and a proximal end 16 joined by a tubular sheath or housing 18 made of an insulating, biocompatible, biostable material such as silicone rubber or polyurethane.

The distal end 14 of the lead body 12 includes a distal tip 19, comprising a tip surface 20 incorporating a pacing/sensing electrode array to be described. Optionally, disposed proximally of the tip surface 20 along the distal end of the lead body is a pacing and/or sensing ring electrode 22.

The proximal end 16 of the lead 10 incorporates a connector assembly 24 for connecting the lead body 12 to a pacemaker and/or ICD 26. The connector assembly 24 includes a tubular, rotatable pin terminal 28 and a pair of ring terminal contacts 30, 32 electrically coupled to the electrodes on the tip surface 20. The connector assembly 24 of the lead is received within a receptacle of the pacemaker/ICD 26 and to prevent ingress of body fluids into the receptacle the connector assembly is provided with spaced sets of seals 34 in accordance with well known arrangements in the art. In accordance with well known implantation techniques, a stylet or guidewire for delivering and steering the distal end 14 of the lead body during implantation is inserted into a lumen of the lead body 12 through the tubular connector pin 28. Further, in accordance with well known techniques, the lead body housing 18 may have a lubricious coating on most or all of its outer surface to facilitate its movement through a delivery introducer and the patient's vascular system.

The distal tip 19 of the lead body includes a fixation means in the form of a helix 36 extended or retracted by means of a rotatable actuator such as a coil 38 coupling the helix 36 with the rotatable tubular pin terminal 28. The lumen of the helix coil 38 may provide a passage for a stylet or guidewire for steering and positioning the distal tip 19 during implantation. In the specific example under consideration, the helix 36 is passive in the sense that it is not electrically active, functioning only to provide for fixation and secure contact between the distal tip surface 20 and the adjacent tissue of the heart. Alternatively, as will be described below, the helix may be conductive along its entire length or along only a portion thereof.

The tip surface 20 carries three "dot" electrodes 40, 42 and 44 having active surface areas and spaced closely together in a clustered array about a central aperture 46 through which the anchoring helix 36 projects when extended. Electrodes 40 and 42 collectively function as an anode; as shown in FIG. 3, these two electrodes are connected in parallel to a single conductor 48 extending the length of the lead body to one of the contacts 30 and 32 on the connector assembly 24. The third electrode 44 on the tip surface 20 functions as a cathode; this electrode is connected to a second conductor 50 extending the length of the lead body and coupled to the other of the contacts 30 and 32. The ring electrode 22 may be used as an anode in combination with the cathode 44 for cardiac pacing or to sense electrical impulses produced by the heart tissue. The cross-sectional configuration of the lead body housing 18 may accommodate various combinations of coil and/or cable conductor combinations including, for example, bipolar coaxial coils or bipolar cables or multilumen combinations of coils and/or cables.

The electrodes 40, 42 and 44 have small active surface areas and are closely spaced so as to simultaneously provide immunity from far field signals and a high pacing impedance. For example, the two anode electrodes 40 and 42 may each have an active surface area of 0.5 mm$^2$ in which case the cathode electrode 44 may have an active surface area of 0.3 mm$^2$. It will thus also be seen that the total surface area of the anode would be about three times that of the cathode which, as indicated, is known in the art to be a desirable anode-to-cathode active surface area ratio. The small electrode active surface areas, such as those mentioned above, can provide a high pacing impedance in the range of 1,500 to 3,000 ohms. The spacing between electrodes may be about 0.3 mm. The electrode "dots" need not be circular. They can have any geometrical shape suitable for use as a pacing and/or sensing electrode, including but not limited to semicircular, square, rectangular, hexagonal, oval, annular, and so forth.

It will be seen that the electrodes 40, 42 and 44 on the tip surface 20 of the lead body are not arranged in a straight line. This nonlinear pattern assures that regardless of the direction of an approaching depolarization wavefront, the cathode electrode 44 and at least one of the anode electrodes 40, 42 will be intercepted in succession so as to produce a robust sensed voltage above the threshold needed to allow appropriate device algorithms to function without confusion. The amplitude of these signals far exceeds that of any unwanted far field signals. Accordingly, a clean, low noise cardiac signal is generated with minimal or no far field signals.

Figure 4:
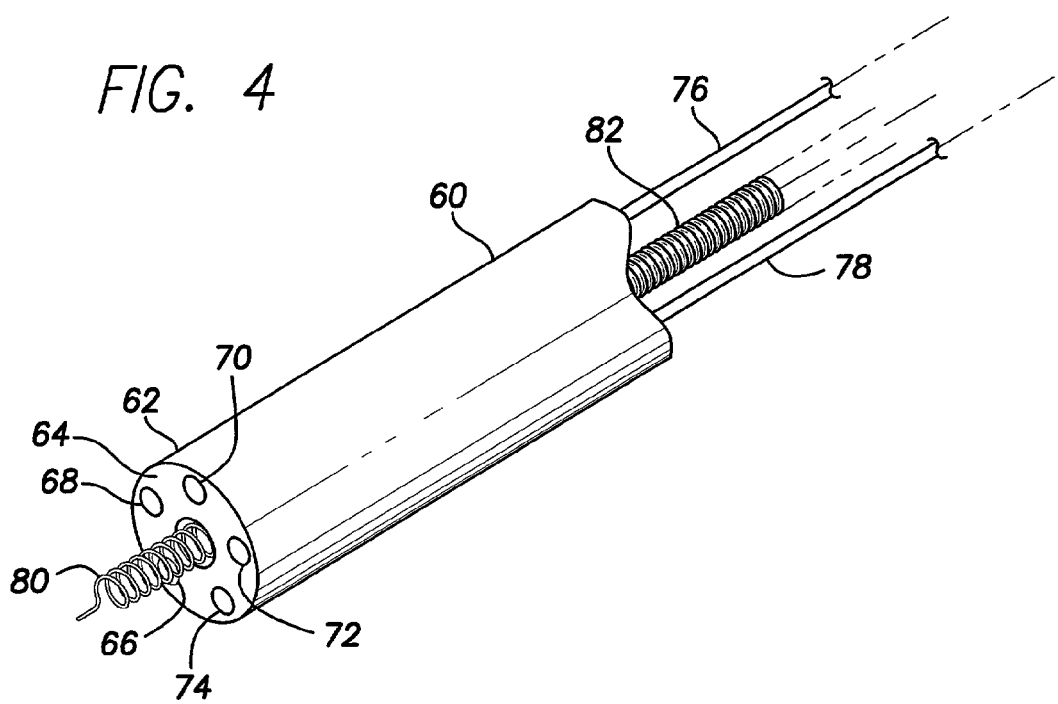
FIG. 4 is a perspective view of a portion of the distal end of a bipolar endocardial pacing and sensing lead having a distal tip incorporating an electrode array in accordance with another embodiment of the present invention.
Figure 5:
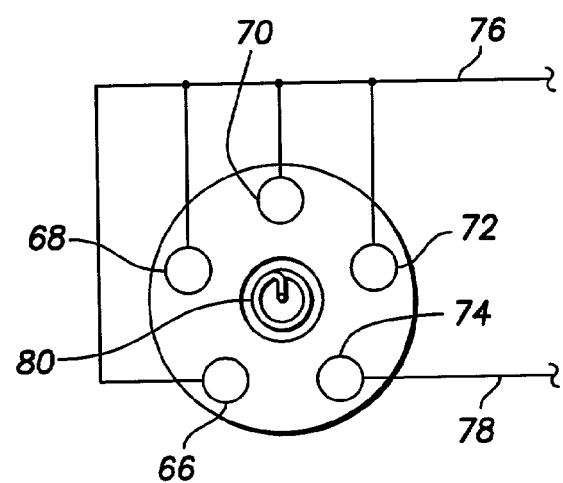
FIG. 5 is a front elevation view of the lead shown in FIG. 4.

FIGS. 4 and 5 show the distal end 60 of a bipolar pacing and sensing body-implantable lead in accordance with another embodiment of the present invention. The distal end 60 of the lead includes a distal tip 62 terminating at a tip surface 64 carrying five electrodes 66, 68, 70, 72 and 74. The four electrodes 66, 68, 70 and 72 collectively function as an anode while the remaining electrode 74 serves as a cathode. As shown in FIG. 5, the four anode electrodes are connected in parallel to a single electrical conductor 76 which, as in the first embodiment, may take the form of a small diameter, closely wound coil of fine wire or, preferably, a multistrand or braided cable, coupling the anode electrodes to a contact on a connector assembly at the proximal end of the lead as previously described. The cathode electrode 74 is connected to a separate, single conductor 78 which also may take the form of either a coil or a multistrand cable conductor.

In the specific embodiment shown in FIGS. 4 and 5, the surface areas of the five electrodes 66, 68, 70, 72 and 74 are all the same; the total active surface area of the four anode electrodes would therefore be about four times that of the active surface area of the single cathode electrode which, as explained, is within the range of desirable anode-to-cathode surface area ratios of about 2:1 to about 6:1. The small surface area, closely spaced electrodes would not generate any significant voltages due to far field artifacts but would produce between the anode electrodes on the one hand and the cathode electrode on the other hand a clean, high amplitude potential from the sensing of local cardiac events, the term "local" meaning in the immediate vicinity of the tip surface.

In addition, as in the first embodiment, given the nonlinear electrode arrangement, an output voltage would invariably be generated regardless of the direction of an approaching depolarization wavefront since the cathode electrode and at least one of the anode electrodes would always be intercepted in succession by the wavefront. In addition, given the small surface areas of the electrodes, high pacing impedances exceeding 1000 ohms, and preferably in the range of 1500 to 3000 ohms, are provided.

As in the first embodiment, the lead of the second embodiment includes an electrically passive fixation helix 80 actuated by a rotatable coil 82. It will be evident that the four anode electrodes could have different surface areas, as could the cathode electrode. Alternatively, three of the five dot electrodes could comprise anodes with the remaining two serving as cathodes; other possible combinations will be apparent to those skilled in the art. Still further, it will be evident to skilled artisans that the total number of electrodes, instead of five, could be three, four, six or even more, connected in various anode and cathode combinations.

Figure 6:
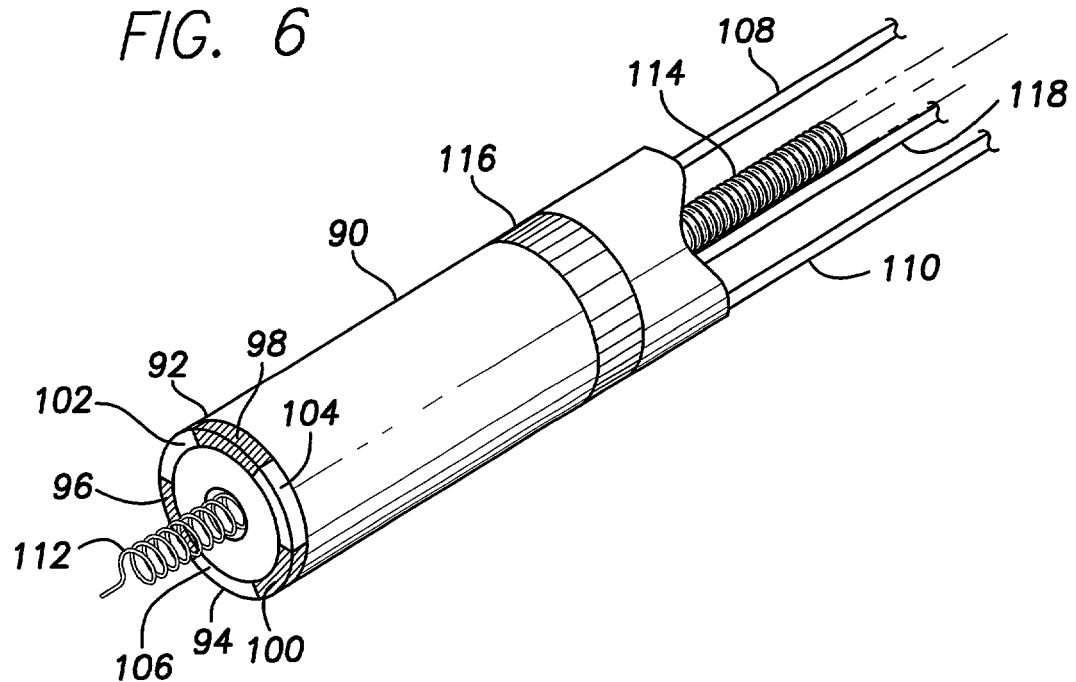
FIG. 6 is a perspective view of the distal end portion of a multipolar lead in accordance with yet another embodiment of the present invention.
Figure 7:
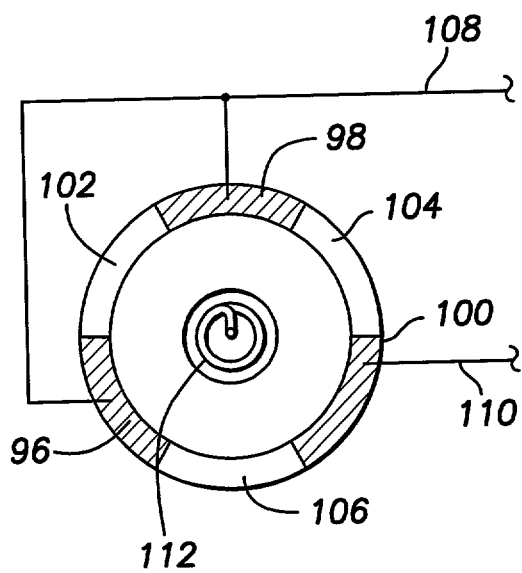
FIG. 7 is a front elevation view of the lead shown in FIG. 6.

With reference now to FIGS. 6 and 7, there is shown the distal end 90 of a bipolar pacing and sensing lead in accordance yet another embodiment of the present invention. The distal end 90 includes a distal tip 92 including a segmented collar 94. In the specific embodiment under consideration, the collar 94 comprises three conductive segments 96, 98 and 100 separated by intervening insulative segments 102, 104 and 106. Two of the conductive segments 96 and 98 function collectively as an anode electrode while the third conductive segment 100 serves as a cathode. As before, the anode electrodes 96 and 98 are parallel-connected to a single conductor 108 coupled to a contact on the connector assembly at the proximal end of the lead. The cathode electrode 100 is similarly connected to a single conductor 110, separate from the first mentioned conductor, and connected to another contact on the connector assembly. As before, the electrical conductors 108, 110 may comprise small coiled conductors of fine, closely wound wire, or cable conductors preferably of the multistrand or braided type.

In the specific embodiment shown in FIGS. 6 and 7, three equiangularly spaced, segment electrodes 96, 98 and 100 subtending equal angles are illustrated. By way of example only and not by way of limitation, the surface area of each of the electrodes 96, 98 and 100 may range from about 0.3 square mm to about 1.5 square mm and the interelectrode spacings may range from about 0.2 mm to about 0.4 mm. It will be obvious, however, that the electrodes may be configured to subtend different angles, and that more than three segmented electrodes may be used. The embodiment shown in FIGS. 6 and 7 may also include a rotatable fixation helix 112 and an associated helix actuator coil 114 along the lines already described. Also, optionally included, is a ring pacing or sensing electrode 116 coupled to a contact assembly by means of a conductor 118.

FIGS. 8–10 show a variation of the bipolar pacing and sensing lead of the embodiment of FIGS. 6 and 7. The lead of FIGS. 8–10 includes a distal end 120 having a distal tip 122 incorporating a segmented collar 124 comprising three conductive segments 126, 128 and 130 separated by intervening insulating segments 132, 134 and 136. The three conductive segments jointly function as an anode and in this respect, as shown in FIG. 9, the three conductive segments 126, 128 and 130 are parallel-connected to a single coil or cable conductor 138 coupled to a terminal contact on the connector assembly (not shown). The distal tip 122 further includes a central aperture 140 through which a rotatable helix 142 may be extended to anchor the distal end 120 of the lead to adjacent tissue. Unlike the helix in the embodiment of FIGS. 6 and 7, the helix 142 is electrically active, functioning as the cathode of the bipolar lead. In this connection, the helix 142 includes an uninsulated or bare mid-section 144 interposed between insulated distal and proximal portions 146 and 148. With the helix 142 extended to anchor the distal end 122 of the lead body in the adjacent heart tissue, electrical contact will be established between the bare mid-section 144 of the helix 142 and the surrounding tissue. It will be evident that instead of a mid-section of the helix being electrically active, an uninsulated distal end section of the helix may be made to comprise the electrically active surface, with the remaining, proximal portion of the helix being electrically insulated. In either case, the helix 142 is mechanically and electrically connected to a coil conductor 150 in turn coupled to a rotatable pin on a connector assembly at the proximal end of the lead, the pin in this case serving also as an electrical terminal contact. By way of example and not limitation, the electrically active surface of the helix 142 may have an area ranging from about 2 square mm to about 8 square mm, and the total surface area of the three anode electrodes 126, 128 and 130 may range from about 4 square mm to about 15 square mm.

Figure 11:
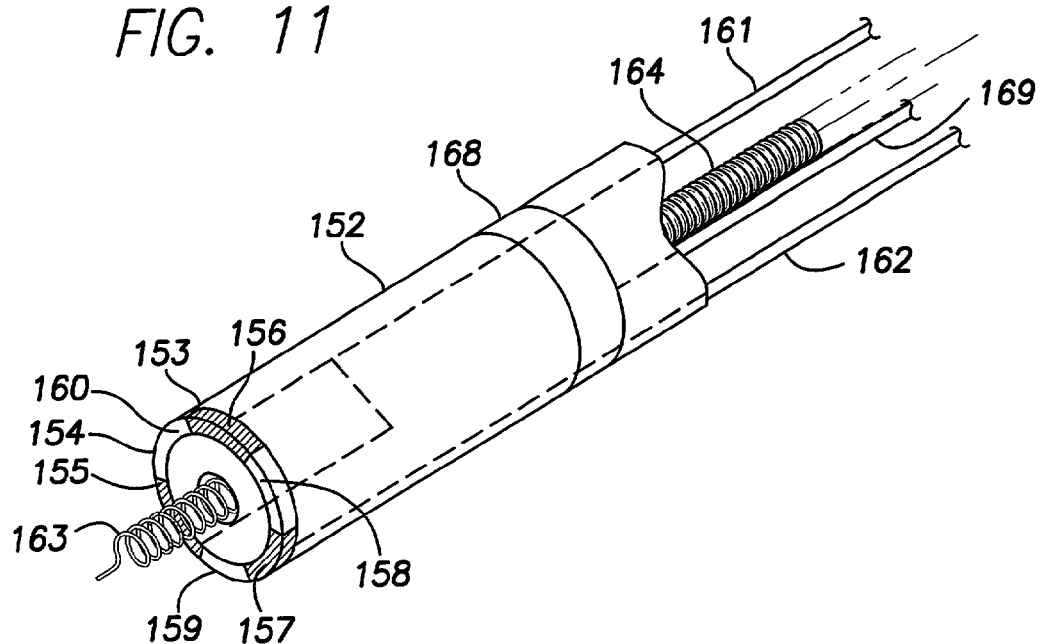
FIG. 11 is a perspective view of a portion of the distal end of a bipolar endocardial pacing and sensing lead having a distal tip incorporating an electrode array in accordance with still another embodiment of the present invention.
Figure 12:
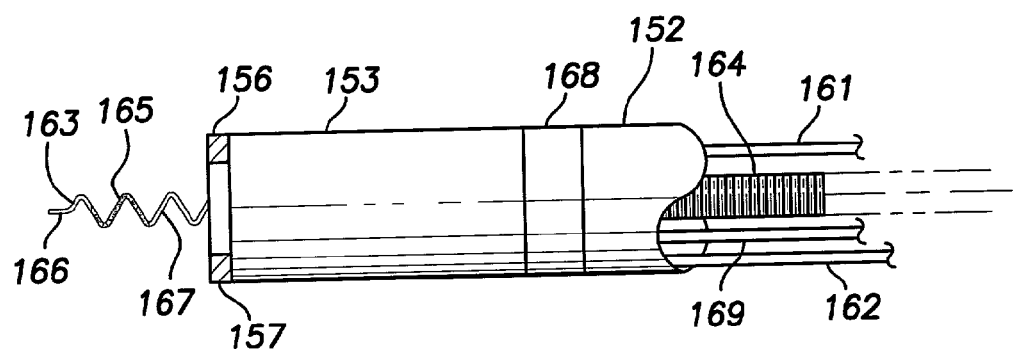
FIG. 12 is a side view of the distal end of the lead shown in FIG.

FIGS. 11 and 12 show another variation of the bipolar pacing and sensing lead of the embodiment of FIGS. 6 and 7. The lead of FIGS. 11 and 12 includes a distal end 152 having a distal tip 153 incorporating a segmented collar 154 comprising, in this specific example, three electrically conductive segments 155–157 separated by intervening insulating segments 158–160. The two conductive segments 155 and 156 together function as an anode electrode and accordingly may be parallel-connected to a single coil or cable conductor 161 coupled to a terminal contact on a proximal connector assembly (not shown). The conductive segment 157 serves as a cathode coupled to a terminal contact on the connector assembly of the lead by means of a coil or cable conductor 162. In accordance with one specific example, the anode pair 155, 156 and the cathode 157 may be used to sense local cardiac electrical activity.

The distal tip 153 further carries a rotatable helix 163 which is extendable by means of a rotatable actuator coil 164 to anchor the distal tip 153 to adjacent body tissue. The helix 163 is electrically active, functioning by way of example as a cathode. In this connection, the helix 163 includes an uninsulated or bare mid-section 165 interposed between insulated helix sections 166 and 167. Electrical pulses applied across the electrically active helix 163 and an anode ring electrode 168 proximal of the segmented collar 154 provide pacing stimuli to the adjacent body tissue. The ring electrode 168 is connected to a terminal contact on the connector assembly via an electrical conductor 169.

It will be evident that instead of the segmented electrodes 155–157, dot electrodes arranged across the distal tip may be used. Further, the helix 163 may be designed so that a distal section thereof, instead of the mid-section 165, is uninsulated so as to present an electrically conductive surface to the surrounding tissue. Desirable anode-to-cathode area ratios, as already described, can be readily provided.

Figure 13:
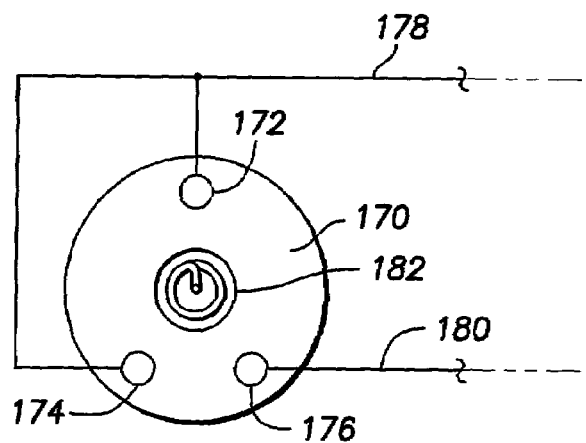
FIGS. 13, 14 and 15 are front elevation views of the distal tips of bipolar endocardial pacing and sensing leads showing further variations of electrode arrays in accordance with the present invention.

FIGS. 13 through 16 illustrate still further variations of bipolar lead electrode arrays in accordance with the present invention. FIG. 13 shows a tip surface 170 carrying three electrodes 172, 174, and 176 having the same surface area. Two of the electrodes 172 and 174 jointly function as an anode, and these electrodes are connected in parallel to a single conductor 178, along the lines already described. The third electrode 176 functions as the cathode and it is connected to a separate conductor 180. A passive helix 182 may be provided for anchoring.

Figure 14:
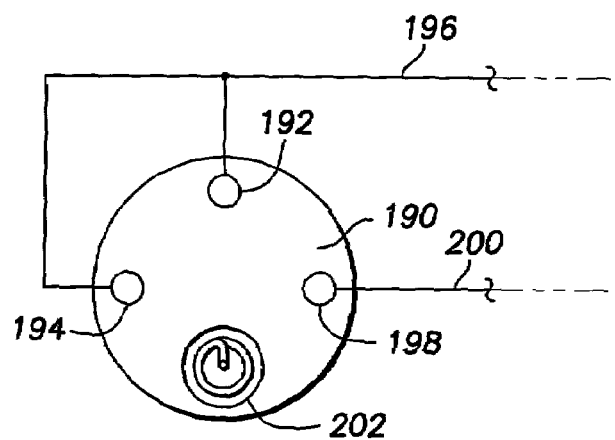

FIG. 14 shows a lead tip surface 190 in accordance with the present invention in which two anode electrodes 192 and 194 commonly connected to a conductor 196, and a third, cathode electrode 198 connected to a conductor 200 occupy a portion of the tip surface. The lead includes an off-center, passive anchoring helix 202. In all other respects, the lead is the same as those already described.

Figure 15:
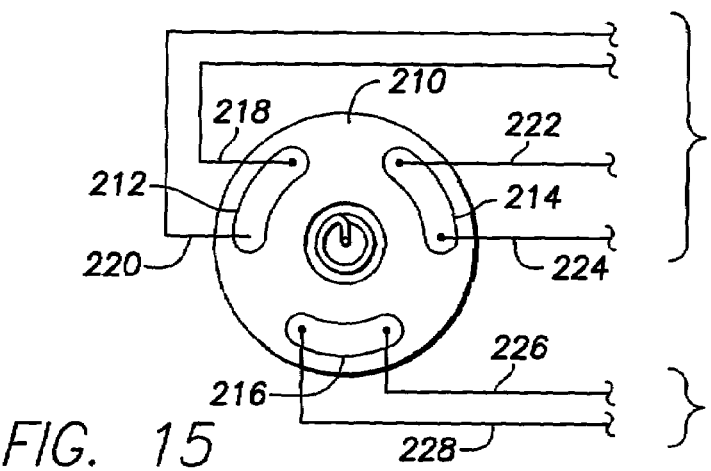

FIG. 15 shows yet another embodiment of the present invention in which a tip surface 210 carries three arcuate electrodes 212, 214 and 216, two of which (212 and 214) jointly function as an anode and the remaining one of which (216) functions as a cathode. For redundancy, each electrode is attached to two multistrand or braided cable conductors. Thus, the anode electrode 212 is connected to a pair of conductors 218, 220; the anode electrode 214 is connected to a pair of conductors 222, 224; and the cathode electrode 216 is connected to a pair of conductors 226, 228. The electrical conductors 218, 220, 222 and 224 connected to the anode electrodes are all connected in parallel to the same terminal contact on a connector assembly on the proximal end of the lead. Similarly, the redundant cathode electrode conductors 226 and 228 are coupled to another terminal contact on the connector assembly. The embodiment of FIG. 15 may also include a fixation helix 230 which may be either electrically active or electrically passive, as already described. Although three arcuate electrodes are illustrated in FIG. 15, it will be obvious that other numbers of electrodes may be utilized so long as the aforedescribed preferable area ratio is observed. Further, although the arcuate electrodes shown in FIG. 15 are arranged concentrically about a central, longitudinal axis of the lead body, it will be evident that this need not be the case.

Figure 16:
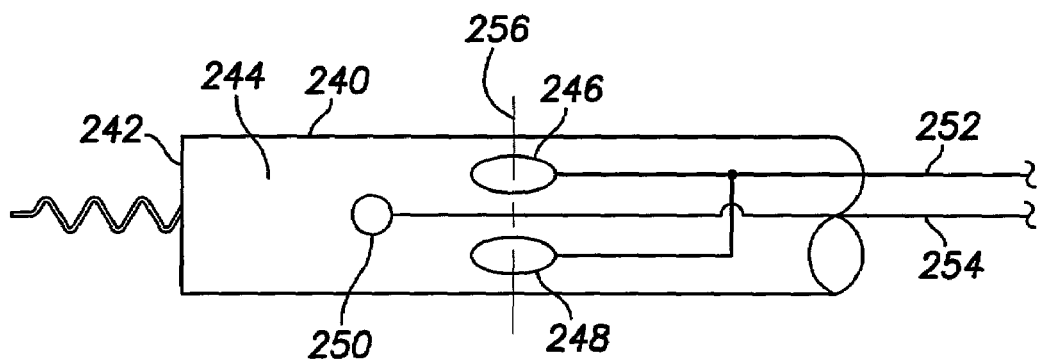
FIG. 16 is a side view of the distal end of a bipolar endocardial pacing and sensing lead including an electrode array disposed on the side surface of the lead in accordance with yet another embodiment of the present invention.

FIG. 16 shows a distal end 240 of a bipolar pacing and sensing lead in accordance with yet another embodiment of the present invention. The distal end 240 terminates in a tip surface 242 and further has a side surface 244, which will typically be substantially cylindrical although it will be evident that the lead body outer surface need not be limited to any particular geometry. The side surface 244 along the distal end of the lead carries an array of three electrodes 246, 248 and 250 which may function as sensing electrodes. The electrodes 246 and 248 serve as anodes and are commonly connected to a single conductor 252 in turn connected to a terminal contact on a connector assembly at the proximal end of the lead. The remaining electrode 250 which can be a dot electrode, as shown, or a full ring electrode, functions as a cathode and is connected by means of a separate conductor 254 to another contact on the connector assembly. In the particular electrode pattern illustrated in FIG. 16, the anode electrodes are disposed along a common transverse plane 256 while the cathode electrode is positioned distally of the plane 256 occupied by the anode electrodes. In this way, a sensed potential will always be generated irrespective of the direction of an incident depolarization wavefront, in the manner already described. Preferably, the surface area of the anode electrodes exceeds that of the cathode electrode also as previously described.

Figure 17:
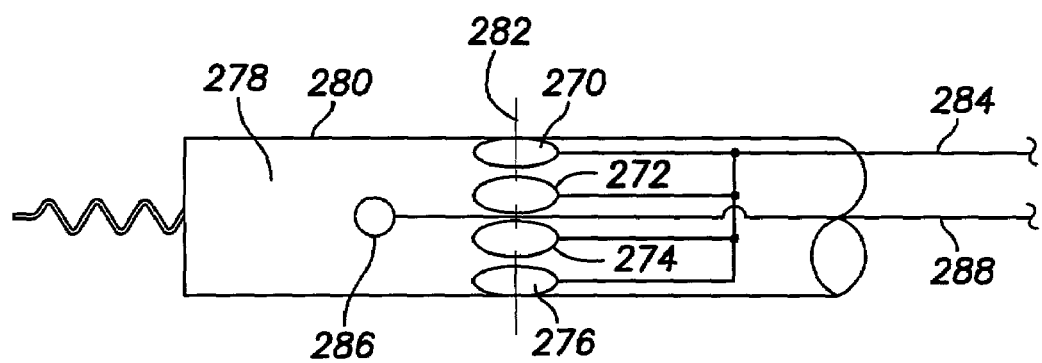
FIG. 17 is a side view of an alternative embodiment of the electrode arrangement on the lead shown in FIG. 16.

FIG. 17 shows a variation of the electrode pattern illustrated in FIG. 16. In the embodiment of FIG. 17, four electrodes 270, 272, 274 and 276, together serving as an anode, are arranged about a side surface 278 of the distal lead end 280. The four electrodes lie along a transverse plane 282. These electrodes are connected in parallel to a single conductor 284. A fifth electrode 286, which may comprise a dot electrode, as shown, or a full ring electrode, serves as the cathode and is disposed distally of the plane 282 of the anode electrode array. As before, the cathode is connected to a separate, single conductor 288.

Figure 18:
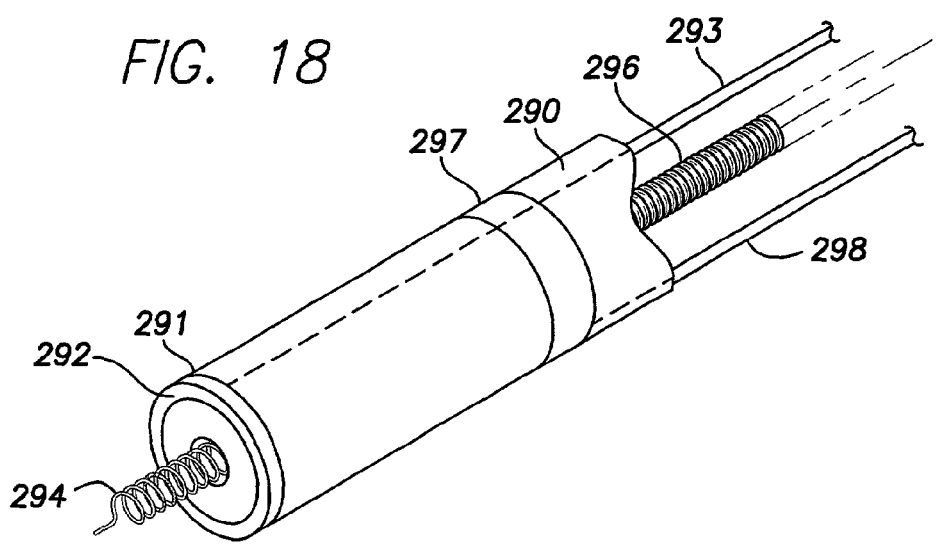
FIG. 18 is a perspective view of a portion of the distal end of a bipolar endocardial pacing and sensing lead having a distal tip incorporating an electrode array in accordance with another embodiment of the present invention.
Figure 19:
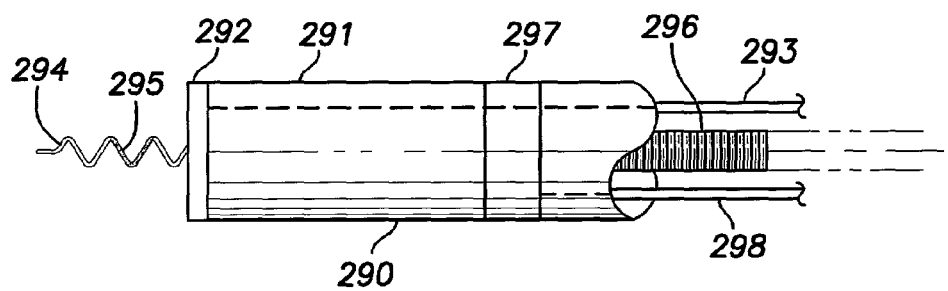
FIG. 19 is a side view of the distal end of the lead shown in FIG. 18.

FIGS. 18 and 19 show the distal end 290 of a bipolar pacing and sensing lead in accordance with yet another specific, exemplary embodiment of the present invention. The distal end 290 includes a distal tip 291 incorporating a non-segmented, that is, a one-piece, electrically conductive collar 292 connected to terminal contact on a connector assembly (not shown) at the proximal end of the lead by means of an electrical coil or cable conductor 293. The distal tip 291 further carries an electrically active fixation helix 294 having a conductive mid-section 295 and coupled by a coil conductor/actuator 296 to a rotatable terminal contact pin forming part of the connector assembly at the proximal end of the lead. As noted earlier, the electrically conductive portion of the helix may be provided along the distal end thereof instead of along the mid-section 295. The distal end 290 of the lead may include, as an option, a conductive ring electrode 297 proximal of the distal tip 291; an electrical conductor 298 connects the ring electrode 297 to another terminal contact on the lead's connector assembly. By way of example and not limitation, pacing and sensing may be performed between the collar 292, functioning as an anode, and the smaller electrically active area of the helix 294 serving as a cathode. When provided, the optional ring electrode 297 may function as an additional, area-increasing anode whose conductor 298 may be connected in parallel with the collar conductor 293.

Figure 20:
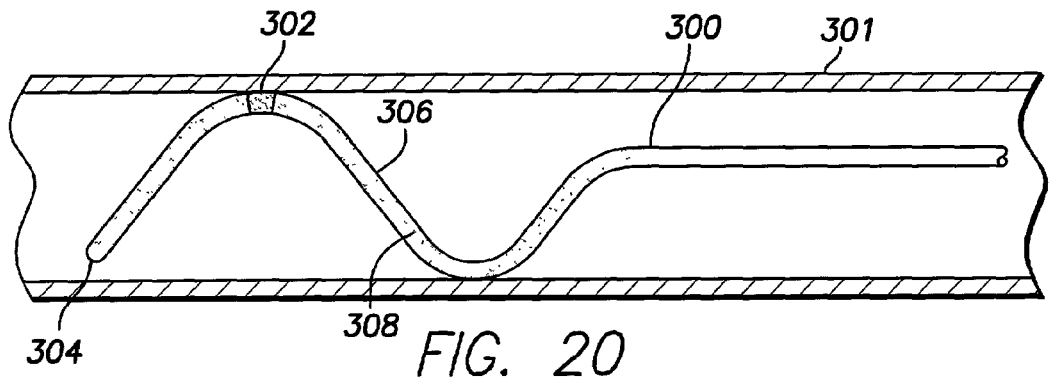
FIG. 20 is a side view of the distal end of a bipolar endocardial pacing and sensing lead in accordance with an alternative embodiment of the invention particularly useful for implantation in the coronary sinus region of the heart for left side stimulation and/or sensing.

With reference to FIG. 20, there is shown the distal end 300 of a lead in accordance with yet another embodiment of the invention particularly suitable for left side placement within a vessel 301 overlying the left side of the heart. For left side placement, a softer, more flexible distal end is preferred with a length corresponding to the coronary sinus and its associated coronary vessels overlying the left side of the heart. In a case in which a sensing electrode such as a ring electrode 302 is provided, it is desirable to have the distance between the tip surface 304 and the ring sensing electrode 302 sufficiently small to allow both of these electrodes to be placed in a target coronary vessel such as the LPV vein. Such placement of the tip and ring electrodes ensures achieving capture of the left ventricle.

The tip surface 304 may include any of the various tip and/or side "dot", collar and/or ring electrode arrays and configurations already described, the essential difference being that the embodiment of FIG. 20 would not include a helix fixation means. Instead, the distal end 300 includes an alternative passive fixation means to help anchor the distal portion of the lead body within a target vessel of the coronary sinus region. The passive fixation or anchoring means may comprise one or more preformed humps, spirals, S-bends or other configurations manufactured into the distal portion of the lead body. In the specific exemplary embodiment shown in FIG. 20, the distal portion of the lead body has a single S-bend 306 so that when the distal end of the lead body is in place within the target coronary vessel 301, there will be biased contact between the S-shaped bend 306 and the inner wall of the vessel 301 so as to create wedging forces sufficient to anchor the lead and prevent its displacement or dislodgment. Ideally, as illustrated in FIG. 20, the distal end 300 is positioned within the vessel 301 so that the ring electrode 302 and the electrode(s) on the tip surface 304 are in intimate electrical communication with the inner wall of the vessel 301. Alternatively, the passive fixation means may comprise—either by itself or in combination with humps, spirals, bends, or the like—one or more soft, flexible protuberances that also tend to wedge the distal portion of the lead body in the target coronary vein. In either case such passive fixation means biases the distal portion against the vessel wall. As further shown in FIG. 20, the passive fixation means can further include texturization 308 of the distal end 300 of the lead body to promote rapid blood clotting and resulting fibrotic tissue growth about the distal portion to help anchor that portion in place.

While several illustrative embodiments of the invention have been shown and described, numerous variations and alternate embodiments will occur to those skilled in the art. For example, it will be obvious that instead of a single cathode electrode as provided in several of the described embodiments, two or more such electrodes may be included. Further, although the tip surfaces shown in certain of the aforedescribed embodiments each lies generally in a plane perpendicular to a central, longitudinal lead axis, it will be obvious that the tip surfaces may be curved, for example, in the shape of a hemispherical surface or other configuration to assure optimal electrical engagement with the cardiac tissue to be stimulated with minimal risk of perforating the tissue engaged by the tip surface. Such variations and alternate embodiments are contemplated, and can be made without departing from the spirit and scope of the invention as defined in the appended claims.

What is claimed is:

1. A body implantable lead for transmitting electrical signals between an electrical connector at a proximal end of the lead and selected body tissue, the electrical connector being adapted to be received by a receptacle in an implantable medical device, the lead comprising:
a lead body having a distal end;
a distal tip surface at the distal end of the lead body, the distal tip surface carrying at least two parallel-connected anode sensing electrodes, and further carrying at least one cathode sensing electrode, the respective electrodes being adapted to electrically communicate with the selected body tissue;
a first conductor electrically coupling the at least two anode sensing electrodes with the connector assembly; and
a second conductor electrically coupling the at least one cathode sensing electrode with the connector assembly;
wherein each of the first and second conductors comprises a pair of redundant conductors.

2. The lead of claim 1 in which:
the respective electrodes are configured and positioned to generate a net voltage output in response to an incident depolarization wavefront, the net voltage output being sufficient to be acknowledged by the implantable medical device.

3. The lead of claim 2 in which:
the respective electrodes are arranged on the distal tip surface so as to generate The net voltage output irrespective of the direction of the incident depolarization wavefront.

4. The lead of claim 1 in which:
the at least two anode sensing electrodes have a total active surface area greater than the total active surface area of the at least one cathode sensing electrode.

5. The lead of claim 4 in which:
the total active surface area of the at least two anode sensing electrodes is at least about twice that of the total active surface area of the at least one cathode sensing electrode.

6. The lead of claim 5 in which:
the total active surface area of the at least two parallel-connected electrodes is at least about 1.0 mm$^2$ and the total active surface area of the at least one additional electrode is about 0.3 mm$^2$.

7. The lead of claim 4 in which:
the active surface area of each of the at least two anode sensing electrodes and the at least one cathode sensing electrode are substantially equal.

8. The lead of claim 1 in which:
all of the electrodes are arranged in a closely spaced cluster so as to sense local electrical events and not far field signals.

9. The lead of claim 1 in which:
the electrodes have active surface areas providing an impedance of at least about 1,500 ohms.

10. The lead of claim 1 in which:
each of the electrodes has a small active surface area, the electrodes being arranged in a closely spaced cluster, the electrodes being substantially non-responsive to far field signals.

11. The lead of claim 1 in which:
the distal end of the lead carries an extendable/retractable screw-in helix for anchoring the distal end in tissue within the right side of the heart.

12. The lead of claim 1 in which:
each of the electrodes comprises a dot electrode.

13. The lead of claim 1 in which:
each of the electrodes comprises a conductive segment of an annular collar mounted on the distal tip surface of the lead.

14. The lead of claim 1 in which:
each of the electrodes has an arcuate configuration.

15. The lead of claim 1 in which:
each conductor of each of the conductor pairs comprises a multistrand cable.

16. The lead of claim 1 in which:
the selected body tissue comprises a heart; and the distal end of the lead is configured to passively anchor the distal end within a coronary vessel overlying the left side of the heart.

17. An implantable stimulation lead for transmitting electrical signals between an implantable medical device and selected body tissue, the lead comprising:
a lead body defining a proximal end carrying a connector assembly connectable to the implantable medical device, the lead body further defining a distal end;
a distal tip surface at the distal end of the lead body, the distal tip surface being substantially perpendicular to a longitudinal axis of the lead body;
at least one cathode sensing electrode at the distal tip surface and adapted to sense local electrical activity manifested by an incident depolarization wavefront;
at least two anode sensing electrodes at the distal tip surface and adapted to sense local electrical activity manifested by an incident depolarization wavefront;
a first electrical conductor enclosed within the housing, the first conductor electrically coupling the at least one cathode sensing electrode with the connector assembly; and
a second electrical conductor enclosed within the housing, the second conductor electrically coupling the at least two anode sensing electrodes with the connector assembly;
wherein the distal end carries an extendable/retractable screw-in helix to anchor the distal end;
wherein the screw-in helix has an electrically conductive portion, a third electrical conductor coupling the screw-in helix to the connector assembly; and
wherein the electrically conductive portion of the screw-in helix is disposed intermediate electrically insulating portions of the helix.

18. The lead of claim 17 in which:
the at least one cathode sensing electrode and the at least two anode sensing electrodes are arranged on the distal tip surface in a non-aligned pattern wherein an output voltage signal of sufficient amplitude to be acknowledged by the implantable medical device is generated between the at least one cathode sensing electrode, on the one hand, and the at least two anode sensing electrodes of, on the other hand, irrespective of the direction of an incident depolarization wavefront.

19. The lead of claim 17 in which:
the at least two anode sensing electrodes collectively comprise an anode.

20. The lead of claim 19 in which:
the at least two anode sensing electrodes have a total surface area greater than the surface area of the least one cathode sensing electrode.

21. The lead of claim 20 in which:
the first mentioned surface area is at least about twice that of the second mentioned surface area.

22. The lead of claim 21 in which:
the first mentioned surface area is about 1.0 square mm and the second mentioned surface area is about 0.3 square mm.

23. The lead of claim 17 in which:
each of the electrodes comprises a dot electrode.

24. The lead of claim 17 in which:
each of the electrodes comprises an arcuate segment.

25. The lead of claim 17 in which:
the electrodes are arranged in a closely spaced cluster.

26. The lead of claim 17 in which:
the electrodes have surface areas providing an impedance of at least about 1,500 ohms.

27. The lead of claim 17 in which:
each of the electrodes has a small surface area, the electrodes being arranged in a closely spaced cluster, the electrodes being substantially non-responsive to far field signals.

28. An implantable stimulation lead for transmitting electrical signals between an implantable medical device and selected body tissue, the lead comprising:
a lead body defining a proximal end carrying a connector assembly connectable to the implantable medical device, the lead body further defining a distal end;
a distal tip surface at the distal end of the lead body, the distal tip surface being substantially perpendicular to a longitudinal axis of the lead body;
at least one cathode sensing electrode at the distal tip surface and adapted to sense local electrical activity manifested by an incident depolarization wavefront;
at least two anode sensing electrodes at the distal tip surface and adapted to sense local electrical activity manifested by an incident depolarization wavefront:
a first electrical conductor enclosed within the housing, the first conductor electrically coupling the at least one cathode sensing electrode with the connector assembly; and
a second electrical conductor enclosed within the housing, the second conductor electrically coupling the at least two anode sensing electrodes with the connector assembly;
wherein the distal end carries an extendable/retractable screw-in helix to anchor the distal end;
wherein the screw-in helix has an electrically conductive portion, a third electrical conductor coupling the screw-in helix to the connector assembly; and
wherein the screw-in helix comprises a distal portion and a proximal portion, the distal portion of the helix comprising the electrically conductive portion of the helix, and the proximal portion of the helix being electrically insulating.

* * * * *